United States Patent [19]

Küber et al.

[11] Patent Number: 5,670,681

[45] Date of Patent: Sep. 23, 1997

[54] PROCESS FOR PREPARING A CARBON-BRIDGED BISCYCLOPENTADIENE COMPOUND

[75] Inventors: Frank Küber, Oberursel; Michael Riedel, Frankfurt, both of Germany

[73] Assignee: Hoechst Aktiengesellschaft, Germany

[21] Appl. No.: 671,956

[22] Filed: Jun. 28, 1996

[30] Foreign Application Priority Data

Jun. 30, 1995 [DE] Germany .................. 195 23 595.9

[51] Int. Cl.$^6$ .................................................. C07F 17/00
[52] U.S. Cl. ................ 556/53; 585/317; 585/318; 585/360; 585/361; 585/428; 585/431
[58] Field of Search ................... 585/360, 361, 585/428, 431, 317, 318; 556/53

[56] References Cited

U.S. PATENT DOCUMENTS

| | | |
|---|---|---|
| 4,892,851 | 1/1990 | Ewen et al. |
| 5,420,320 | 5/1995 | Zenk et al. ................ 556/53 X |
| 5,474,716 | 12/1995 | Lisowsky ................ 556/53 X |
| 5,569,746 | 10/1996 | Lee et al. ................ 556/43 X |
| 5,578,741 | 11/1996 | Frey et al. ................ 585/360 |
| 5,585,508 | 12/1996 | Kuber et al. ................ 556/53 X |

FOREIGN PATENT DOCUMENTS

| 2024718 | 3/1991 | Canada. |
|---|---|---|
| 0 416 566 | 3/1991 | European Pat. Off.. |

OTHER PUBLICATIONS

Halterman, "Synthesis and Applications of Chiral Cyclopentadienylmetal Complexes", Chem. Rev. 1992, vol. 92, No. 5 pp. 965–994.

Ilya E. Nifant'ev et al. "A New Convenient Route to Substituted 2,2-Biscyclopentdienylpropanes" Chem. Research (S), 1992, p. 162.

*Primary Examiner*—Paul F. Shaver
*Attorney, Agent, or Firm*—Connolly & Hutz

[57] ABSTRACT

The present invention relates to a process for preparing a carbon-bridged biscyclopentadiene compound by reacting one or two cyclopentadiene compounds LH with a carbonyl compound in the presence of at least one base and at least one phase transfer catalyst.

18 Claims, No Drawings

PROCESS FOR PREPARING A CARBON-BRIDGED BISCYCLOPENTADIENE COMPOUND

The present invention relates to a process for preparing a carbon-bridged biscyclopentadiene compound and the use of this process as a substep in the preparation of a carbon-bridged biscyclopentadienyl metallocene which can be used as a catalyst component, e.g. for the preparation of polyolefins.

It is known from the literature that polyolefins can be prepared in the presence of metallocenes in combination with aluminoxanes or other cocatalysts which, owing to their Lewis acidity, can convert the neutral metallocene into a cation and stabilize it.

Metallocenes and semisandwich complexes are of great interest not only in respect of the polymerization or oligomerization of olefins, but they can also be used as hydrogenation, epoxidation, isomerization and C—C coupling catalysts (Chem. Rev. 1992, 92, 965–994).

Carbon-bridged metallocenes are described in the literature (U.S. Pat. No. 4,892,851; EP 416 566). the synthesis of these metallocenes proceeds via the preparation of the carbon-bridged biscyclopentadiene ligand system which has to be carried out in a number of stages and proceeds only in a very small yields.

EP 456 455 discloses the use of quaternary ammonium compounds in the alkylation of cyclopentadienes.

Organometallics, 10, 1991, pages 3739–3745 discloses the use of triethylbenzylammonium chloride in the synthesis of biscyclopentadienyl dimethylmethane.

It is known from the literature that cyclopentadiene can be reacted directly with cyclic ketones, with addition of a base, to give a bridged biscyclopentadiene ligand (J. Chem. Research (S), 1992, 162). This synthesis proceeds in low yield and subsequently requires a complicated chromatographic purification.

It is therefore an object of the invention to provide a preparative process for carbon-bridged biscyclopentadiene compounds which avoids the disadvantages of the prior art.

The present invention accordingly provides a process for preparing a carbon-bridged biscyclopentadiene compound by reacting one or two cyclopentadiene compounds LH, of which at least one cyclopentadiene compound is a substituted cyclopentadiene compound, with a carbonyl compound in the presence if at least one base and at least one phase transfer catalyst.

The carbon-bridged biscyclopentadiene compound preferably has the formula I

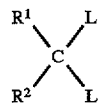
(I)

where L are, independently of one another, identical or different cyclopentadiene groups, where at least one group L is a substituted cyclopentadienyl group, and $R^1$ and $R^2$ are identical or different and are each a hydrogen atom or a $C_1$–$C_{30}$-hydrocarbon radical.

The cyclopentadiene groups L in formula I can be unsubstituted or substituted. They are identical or different, preferably identical.

Examples of substituted cyclopentadiene groups L are: tetramethylcyclopendantadiene, 3-methylcyclopentadiene, 3-tert-butylcyclopentadiene, methyl-tert-butylcyclopentadiene, isopropylcyclopentadiene, dimethylcyclopentadiene, trimethylcyclopentadiene, trimethylethylcyclopentadiene, 3-phenylcyclopentadiene, diphenylcyclopentadiene, indene, 2-methylindene, 2-ethylindene, 3-methylindene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenaphthindene, 2-methyl-4,6-diisopropylindene, fluorene, 2-methylfluorene or 2,7-di-tert-butylfluorene.

One or both of the cyclopentadiene groups L is a substituted cyclopentadiene group, in particular an indene derivative such as indene, 2-methylindene, 2-ethylindene, 3-methylindene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenanaphthindene, 2-methyl-4,6-diisopropylindene or a fluorenyl derivative such as fluorene, 2-methylfluorene or 2,7-di-tert-butylfluorene.

The radical $R^1$ and $R^2$ are identical or different, preferably identical, and are $C_1$–$C_{30}$-hydrocarbon radicals such as $C_1$–$C_{10}$-alkyl or $C_6$–$C_{14}$-aryl. The radicals $R^1$ and $R^2$ can also, together with the atoms connecting them, form a ring system which preferably contains from 4 to 40, particularly preferably from 5 to 15, carbon atoms.

Examples of carbon-bridged biscyclopentadiene compounds of the formula I are:
2,2-bisindenylpropane, 2,2-bisindenylbutane, 2,2-bisindenylmethane, 2,2-bisindenylcyclopentane, 2,2-bisindenylcyclohexane, 1,1-bisindenyl- 1-phenyl-ethane, 1,1-bisindenylethane, 1,1-bisindenylpropane, 2,2-bis(2'-methyl-4'-phenylindenyl)propane, 2,2-bis(2'-ethyl-4'-phenyl-indenyl)propane, 2,2-bis(2'-methyl-4'-naphthylindenyl)propane, 2,2-bis(2'-methyl-4',5'-benzoindenyl)propane, 1,1-bis(2'-methyl-4'-phenylindenyl)-1-phenylethane, 1,1-bis(2'-ethyl-4'-phenyl-indenyl)-1-phenylethane, 1,1-bis(2'-methyl-4'-naphthylindenyl)-1-phenylethane, 2,2-biscyclopentadienylbutane, 2,2-bis(methylcyclopentadienyl)propane, 2-cyclopentadienyl-2-fluorenylpropane, 2-(3'-methylcyclopentadienyl)-2-fluorenylpropane, 2-indenyl-2-indenylfluorenylpropane, 2-cyclopentadienyl-2-indenylpropane, 1-cyclo-pentadienyl-1-fluorenyl-1-phenylethane, 1-indenyl-1-fluorenyl-1-phenylethane, 2-(3'-tert-butylcyclopentadienyl)-2-fluorenylpropane, 1-cyclopentadienyl-1-indenyl-1-phenylethane.

To prepare biscyclopentadiene compounds of the formula I, in which the two cyclopentadiene groups L are identical, use is made of one cyclopentadiene compound LH. To prepare biscyclopentadiene compounds of the formula I, in which the two cyclopentadiene groups L are different, two different cyclopentadiene compounds LH are used.

The cyclopentadiene compounds LH used in the process of the invention can be substituted or unsubstituted, with at least one cyclopentadiene compound being a substituted cyclopentadiene compound.

Examples of substituted cyclopentadiene compounds LH are tetramethylcyclopentadiene, methylcyclopentadiene, tert-butylcyclopenta-diene, methyl-tert-butylcyclopentadiene, isopropylcyclopentadiene, dimethylcyclopentadiene, trimethylcyclopentadiene, trimethylethylcyclo-pentadiene, phenylcyclopentadiene, diphenylcyclopentadiene, indene, 2-methylindene, 2-ethylindene, 3-methylindene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindnene, 2-methyl-4,5-benzoindene, 2-methyl-α-acenaphthindene, 2-methyl-4,6-diisopropylindene, fluorene, 2-methylfluorene or 2,7-di-tert-butylfluorene.

One or both of the cyclopentadiene compounds LH used in the process of the invention is a substituted cyclopentadiene compound, in particular an indene derivative such as indene, 2-methylindene, 2-ethylindene, 3-methylindene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenanaphthindene, 2-methyl-4,6-diisopropylindene or a fluorenyl derivative such as fluorene, 2-methylfluorene or 2,7-di-tert-butylfluorene.

The carbonyl compounds used in the process of the invention are preferably ketones such as acetone, acetophenone, benzophenone, cyclo-hexanone, cyclopentanone, 2-hexanone, 2-butanone, 2-methyl-3-pentanone or 2,2-dimethyl-3-butanone or aldehydes such as acetaldehyde or benzaldehyde.

Bases which can be used are hydroxides of group Ia, IIa or IIIa of the Periodic Table of the Elements, for example LiOH, NaOH, KOH, RbOH, Mg(OH)$_2$, Ca(OH)$_2$ and Sr(OH)$_2$. Preference is given to using one base, e.g. LiOH, NaOH or KOH.

Phase transfer catalysts which can be used are quaternary ammonium salts and phosphonium salts of the formula [R$^3_4$Z]$^+$X$^-$, where R$^3$ are identical or different and are each a hydrogen atom, a halogen atom or a C$_1$–C$_{40}$-group such as a C$_1$–C$_{20}$-alkyl group, a C$_1$–C$_{10}$-alkoxy group, a C$_6$–C$_{20}$-aryl group, a C$_2$–C$_{12}$-alkenyl group, a C$_7$–C$_{40}$-arylalkyl group, a C$_7$–C$_{40}$-alkylaryl group, or a C$_8$–C$_{40}$-arylalkenyl group, which can each bear radicals such as —NR$^4_3$, —SR$^4_2$, —SiR$^4_3$ or —OSiR$^4_3$, where R$^4$ are identical or different and are each a halogen atom, a C$_1$–C$_{10}$-alkyl group or a C$_6$–C$_{10}$-aryl group, or two or more radicals R$^3$ together with the atoms connecting them can form a ring system which preferably contains from 4 to 40, particularly preferably from 5 to 15, carbon atoms, Z is nitrogen or phosphorus and X$^-$ is a halide, hydroxide, tetrahaloborate, (e.g. tetrafluoroborate), hydrogensulfate, sulfate or hexahalophosphate, (e.g. hexafluorophosphate).

Examples of compounds suitable as phase transfer catalysts are:
benzyltrimethylammonium chloride,
benzyltrimethylammonium hydroxide (in particular as an aqueous 40% strength solution),
hexadecyltrimethylammonium bromide,
hexadecyltrimethylammonium chloride (in particular as an aqueous 50% strength solution),
ethylhexadecyldimethylammonium bromixe,
tetraethylammonium tetrafluoroborate,
tetraethylammonium bromide,
tetraethylammonium hydroxide (in particular as an aqueous 20% strength solution),
benzyltriethylammonium chloride,
benzyltriethylammonium hydroxide,
tetrapropylammonium bromide,
tetrabutylammonium chloride,
tetrabutylammonium fluoridetrihydrate,
tetrabutylammonium tetrafluoroborate,
tetrabutylammonium hydrogensulfate,
tetrabutylammonium hydroxide (in particular as a 12.5% strength solution in methanol),
benzeltributylammonium bromide,
tetraoctylammonium bromide,
methyltrioctylammonium chloride,
tetrabutylphosphonium bromide,
tetrabutylphosphonium chloride,
tributylhexadecylphosphonium bromide,
ethyltrioctylphosphonium bromide,
butyltriphenylphosphonium chloride and tetraphenylphosphonium bromide.

Further phase transfer catalysts which can be used are crown compounds, in particular those of the formulae II, III and IV

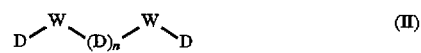 (II)

 (III)

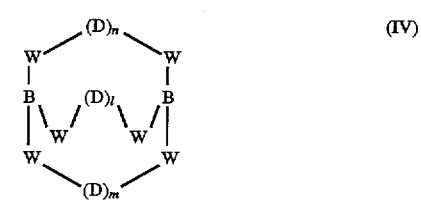 (IV)

where D is S, O, NR$^5$, k PR$^5$ and R$^5$ are identical or different and are each a hydrogen atom, a halogen atom, a C$_1$–C$_{40}$-group such as a C$_1$–C$_{20}$-alkyl group, a C$_1$–C$_{10}$-alkoxy group, a C$_6$–C$_{20}$-aryl group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, which can each bear radicals —NR$^6_3$, —SR$^6_2$, —SiR$^6_3$ or —OSiR$^6_3$ where R$^6$ are identical or different and are each a halogen atom, a C$_1$–C$_{10}$-alkyl group or a C$_6$–C$_{10}$-aryl group, W are identical or different moieties [R$^7_2$C]$_n$, where R$^7$ are identical or different and are each a hydrogen atom, a halogen atom, a C$_1$–C$_{40}$-group such as a C$_1$–C$_{20}$-alkyl group, a C$_1$–C$_{10}$-alkoxy group, a C$_6$–C$_{20}$-aryl group, a C$_2$–C$_{12}$-alkenyl group, a C$_7$–C$_{40}$-arylalkyl group, a C$_7$–C$_{40}$-alkylaryl group, or a C$_8$–C$_{40}$-arylalkenyl group, which can each bear radicals —NR$^8_3$, —SR$^8_2$, —SiR$^8_3$ or —OSiR$^8_3$, where R$^8$ is a halogen atom, a C$_1$–C$_{10}$-alkyl group or a C$_6$–C$_{10}$-aryl group, or two or more radicals R$^7$ together with the atoms connecting them can form a ring system which preferably contains from 4 to 40, particularly preferably from 5 to 15, atoms, in particular carbon atoms, n, l and m are identical or different and are each an integer from 1 to 40, preferably from 1 to 5, and are preferably identical, and B are identical or different and are NR$^9$ or PR$^9$, where R$^9$ is a hydrogen atom, a halogen atom or a C$_1$–C$_{40}$-group such as a C$_1$–C$_{20}$-alkyl group, a C$_1$–C$_{10}$-alkoxy group, a C$_6$–C$_{20}$-aryl group, a C$_2$–C$_{12}$-alkenyl group, a C$_7$–C$_{40}$-arylalkyl group, a C$_7$–CF$_{40}$-alkylaryl group, or a C$_8$–C$_{40}$-arylalkenyl group, which can bear radicals —NR$^{10}_3$, —SR$^{10}_2$, —SiR$^{10}_3$, —OSiR$^{10}_3$, where R$^{10}$ is a halogen atom, a C$_1$–C$_{10}$-alkyl group or a C$_6$–C$_{10}$-aryl group.

Examples of crown compounds are:
12-crown-4, 15-crown-5, benzo-15-crown-5, 18-crown-6, decyl-18-crown-6, dibenzo-18-crown-6, dicyclohexyl-18-crown-8, dibenzo-24-crown-8, (+)-18-crown-6-tetracarboxylic acid, N-phenylaza-15-crown-5, ®Kryptofix 21, ®Kryptofix 22, ®Kryptofix 22 DD, ®Kryptofix 23, tris[2-(-methoxethoxy)-ethyl]amine, ®Kryptofix 5, ®Kryptofix 111, ®Kryptofix 211, ®Kryptofix 221, ®Kryptofix 221 D, ®Kryptofix 222, ®Kryptofix 222 B (50% strength solution in toluene), ®Kryptofix 222 BB, ®Kryptofix 222 CC (50% strength solution in toluene), ®Kryptofix 222 D (50% strength solution in toluene), ®Kryptofix 221 B (polymer), and ®Kryptofix 222 B (polymer).

In the process of the invention, preference is given to using a phase transfer catalyst. The concentration of the phase transfer catalyst can be from 0.1 to 100 mol % based on the amount of cyclopentadiene compound(s) LH used, particularly preferably from 1 to 20 mol %.

The process of the invention is carried out in a single-phase or multiphase system in the presence of at least one base and at least one phase transfer catalyst. The process of the invention is preferably carried out in a multiphase system, in particular in a two-phase system where one phase is an organic solvent, e.g. an aromatic solvent such as toluene, xylene or an aliphatic solvent such as tetrahydrofuran, hexane or dichloromethane, and the second phase is water. Particular preference is given to the two-phase systems toluene/water, dichloromethane/water and tetrahydrofuran/water. The concentration of base in the aqueous phase can be between 5 and 70% by weight, preferably from 25 to 60% by weight.

To synthesize carbon-bridged biscyclopentadiene compounds containing two identical cyclopentadiene groups L, the cyclopentadiene compound LH can be used in excess (based on the carbonyl compound), preference is given to using from 2 to 3 equivalents of the cyclopentadiene compound LH, based on the carbonyl compound used (e.g. acetone or acetophenone). In the synthesis of carbon-bridged biscyclopentadiene compounds containing two different cyclopentadiene groups L, two different cyclopentadiene compounds LH are used. In this case, one of the two cyclopentadiene compounds is first reacted with the carbonyl compound, with the ratio of the two components being approximately 1:1. After a reaction time, which can be between 30 minutes and 100 hours, preferably between 30 minutes and 20 hours, the second cyclopentadiene compound is added.

The reaction temperature can be between 0° C. and 100° C., preferably from 0° C. to 30° C. The reaction times are generally between 30 minutes and 100 hours, preferably between 30 minutes and 20 hours.

The volume ratio of organic phase/water (e.g. toluene/water, dichloromethane/water or tetrahydrofuran/water) can be between 10000:1 and 1:50, preferably between 100:1 and 1:10, particularly preferably between 10:1 and 1:.

Preferably, a mixture of the cyclopentadiene compound LH and the carbonyl compound is initially charged in the organic solvent and the aqueous phase containing both the base and the phase transfer catalyst is added. It is also possible to carry out the reaction the other way around. Furthermore, the carbonyl compound can be added dropwise over a period of from 1 minute to 100 hours, preferably from 15 minutes to 4 hours, to the two-phase system (e.g. toluene/water, dichloromethane/water or tetrahydrofuran/water) containing the cyclopentadiene compound LH, the base and the phase transfer catalyst.

The carbon-bridged biscyclopentadiene compounds obtainable using the process of the invention can be formed as double-bond isomers.

The process of the invention is notable, in particular, for the fact that carbon-bridged biscyclopentadiene compounds can be obtained in a simple, single-stage synthesis in high yield. The substitution pattern of the bridge ($R^1R^2C$) and of the cyclopentadiene groups L can be varied within a wide range.

The present invention also provides for the use of the process of the invention as a substep of a process for preparing a carbon-bridged biscyclopentadienyl metallocene, in particular a carbon-bridged biscyclopentadienyl metallocene of the formula V

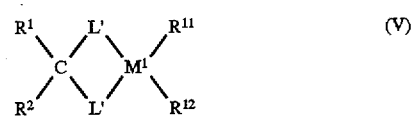

where $M^1$ is an element of group IIb, IVb, Vb or VIb of the Periodic Table of the Elements, in particular of group IVb. where L' are, independently of one another, identical or different cyclopentadienyl groups, where at least one cyclopentadiene group L' is a substituted cyclopentadiene group, $R^1$ and $R^2$ are identical or different and are each hydrogen or a $C_1$–$C_{30}$ hydrocarbon radical such as $C_1$–$C_{10}$-alkyl or $C_6$–$C_{14}$-aryl, the radicals $R^1$ and $R^2$ together with the atoms connecting them form a ring system which preferably contains from 4 to 40, particularly preferably from 5 to 15, carbon atoms, and $R^{11}$ and $R^{12}$ are identical or different and are each hydrogen, a halogen atom or a $C_1$–$C_{40}$-radical such as $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl, $C_8$–$C_{40}$-arylalkenyl, hydroxy, $NR^5,_2$ where $R^5$ is $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl.

The cyclopentadienyl groups L' in formula V can be unsubstituted or substituted. They are identical or different, preferably identical.

Examples of substituted cyclopentadienyl groups L' are: tetramethylcyclopentadienyl, 3-methylcyclopentadienyl, 3-tert-butylcyclopentadienyl, methyl-tert-butylcyclopentadienyl, isopropylcyclopentadienyl, dimethylcyclopentadienyl, trimethylcyclopentadienyl, trimethylethylcyclopentadienyl, 3-phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-a-acenanaphthindenyl, 2-methyl-4,6-diisopropylindenyl, fluorenyl, 2-methylfluorenyl or 2,7-di-tert-butylfluorenyl.

One or both cyclopentadienyl groups L' is a substituted cyclopentadienyl group, in particular an indenyl derivative such as indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-mthyl-4-isopropylindenyl, benzoindenyl, 2-methyl-4,5-benzoindenyl, 2-methyl-α-acenanaphthindenyl, 2-methyl-4,6-diisopropylindenyl or a fluorenyl derivative such as fluorenyl, 2-methylfluorenyl or 2,7-di-tert-butylfluorenyl.

The radicals $R^1$ and $R^2$ are identical or different, preferably identical, and are $C_1$–$C_{30}$-hydrocarbon radicals such as $C_1$–$C_{10}$-alkyl or $C_6$–$C_{14}$-aryl. The radicals $R^1$ and $R^2$ can also, together with the atoms connecting them, form a ring system which preferably contains from 4 to 40, particularly preferably from 5 to 15, carbon atoms.

Preferably $M^1$ is an element of group IV of the Periodic Table of the Elements, for example titanium, zirconium or hafnium, in particular zirconium, $R^1$ and $R^2$ are identical or different, preferably identical, and are hydrogen, $C_1$–$C_{10}$-alkyl or $C_6$–$C_{14}$-aryl, in particular $C_1$–$C_5$-alkyl, and the radicals $R^{11}$ and $R^{12}$ are preferably identical and are $C_1$–$C_4$-alkyl such as methyl or a halogen atom such as chlorine.

Examples of carbon-bridged biscyclopentadienyl metallocenes obtainable by the metallocene preparation process of the invention are:

isopropylinidenebis (2,3,4,5-tetramethylcyclopentadienyl) zirconium dichloride,
methylnaphthylmethylenebis (2,3,4-trimethylcyclopentadienyl)zirconium dichloride,
diphenylmethylenebis (2,3,4,5-tetramethylcyclopentadienyl)dimethyl-zirconium,
methylenebis(1-indenyl)zirconium dichloride,
isopropylidenebis(1-indenyl)zirconium dichloride,
methylphenylmethylenebis(1-indenyl)zirconium dichloride,
diphenylmethylenebis(1-indenyl)zirconium dichloride,
methylenebis(1-(4-phenylindenyl))zirconium dichloride,
isopropylidenebis(1-(4-phenylindenyl))zirconium dichloride,
isopropylidenebis(1-(4-naphthylindenyl))zirconium chloride,
methylphenylmethylenebis(1-(4-phenylindenyl))zirconium dichloride,
diphenylmethylenebis(1-(4-phenylindenyl))zirconium dichloride,
methylenebis(1-(4-isopropylindenyl))zirconium dichloride,
isopropylidenebis(1-(4-isopropylindenyl))zirconium dichloride,
methylphenylmethylenebis(1-(4-isopropylindenyl)) dimethylzirconium,
diphenylmethylenebis(1-(4-isopropylindenyl))hafnium dichloride,
methylenebis(1-(4,5-benzoindenyl))zirconium dichloride,
isopropylidenebis(1-(4,5-benzoindenyl)zirconium dichloride,
methylphenylmethylenebis(1-(4,5-benzoindenyl)) zirconium dichloride,
diphenylmethylenebis(1-(4,5-benzoindenyl))zirconium dichloride,
isopropylidene(1-indenyl)(cyclopentadienyl)zirconium dichloride,
isopropylidene(1-indenyl)(3-methylcyclopentadienyl) zirconium dichloride,
methylphenylmethylene(1-indenyl)(cyclopentadienyl)-zirconium dichloride,
diphenylmethylene(1-indenyl)(cyclopentadienyl)zirconium dichloride,
diphenylmethylene(1-(4-isopropyl)indenyl)(cyclopentadienyl)zirconium dichloride,
isopropylidene(1-indenyl)(cyclopentadienyl)titanium dichloride,
isopropylidene(1-indenyl)(3-methylcyclopentadienyl)-titanium dichloride,
methylphenylmethylene(1-indenyl)(cyclopentadienyl)-titanium dichloride,
diphenylmethylene(1-indenyl)(cyclopentadienyl)titanium dichloride,
isopropylidene(1-indenyl)(9-fluorenyl)zirconium dichloride,
isopropylidene(9-fluorenyl)(3-methylcyclopentadienyl)-zirconium dichloride,
isopropylidene(9-fluorenyl)(3-tert-butylcyclopentadienyl) zirconium dichloride,
methylphenylmethylene(9-fluorenyl)(cyclopentadienyl)-zirconium dichloride,
diphenylmethylene(9-fluorenyl)(cyclopentadienyl)-zirconium dichloride,
diphenylmethylene(9-fluorenyl)(3-phenylcyclopentadienyl) zirconium dichloride,
diphenylmethylene(1-(4-isopropyl)indenyl)(9-fluorenyl)-zirconium dichloride,
isopropylident(9-fluorenyl)(cyclopentadienyl)zirconium dichloride,
methylphenylmethylene(9-fluorenyl)(cyclopentadienyl)-titanium dichloride,
diphenylmethylene(9-fluorenyl)(cyclopentadienyl)-dimethyltitanium,
diphenylmethylene(9-(2,7-di-tert-butyl)fluorenyl) (cyclopentadienyl)zirconium dichloride,
isopropylidene (9-(2,7-di-tert-butyl)fluorenyl)-(cyclopentadienyl)zirconium dichloride.

The present invention thus also provides a process for preparing a carbon-bridged biscyclopentadienyl metallocene, comprising the steps:

a) Reacting one or two cyclopentadiene compounds LH, of which at least one cyclopentadiene compound is a substituted cyclopentadiene compound, with a carbonyl compound in the presence of at least one base and at least one phase transfer catalyst to give a carbon-bridged biscyclopentadiene compound, and b) Reacting the carbon-bridged biscyclopentadiene compound obtained in step a) with a metal compound $M^1X_p$, where $M^1$ is an element of group IIIb, IVb, Vb or VIb of the Periodic Table of the Elements, X is a $C_1$–$C_{40}$-radical such as $C_1$–$C_{10}$-alkyl or $NR^{13}{}_2$, where $R^{13}$ is a $C_1$–$C_{20}$-hydrocarbon radical such as $C_1$–$C_{10}$-alkyl or $C_6$–$C_{16}$-aryl, a halogen or a pseudohalogen and p is an integer from 0 to 4, under conditions under which the carbon-bridged biscyclopentadiene compound obtained in step a) is complexed to give the carbon-bridged biscyclopentadienyl metallocene.

The second step (b) of the preparative process for the carbon-bridged biscyclopentadienyl metallocene can be carried out by literature method (e.g. AU-A-31478/89; J. Organomet. Chem. 1988, 342, 21 or EP-A 284 707, which are hereby expressly incorporated by reference). The carbon-bridged biscyclopentadiene compound is preferably first reacted with a compound of the formula $R^{14}M^2$ where $M^2$ is a metal of group Ia, IIa or IIIa of the Periodic Table of the Elements and $R^{14}$ is a $C_1$–$C_{20}$-hydrocarbon radical such as $C_1$–$C_{10}$-alkyl or $C_6$–$C_{14}$-aryl, and subsequently with the metal compound $M^1X_p$. The reactions preferably take place in a suitable solvent, e.g. an aliphatic or aromatic solvent such as hexane or toluene, an ether solvent such as tetrahydrofuran or diethyl ether or in halogenated hydrocarbons such as methylene chloride or o-dichlorobenzene. In the metal compound of the formula $M^1X_p$, $M^1$ is preferably an element of group IIIb of the Periodic Table of the Elements, X is preferably a halogen atom or $NR^{13}{}_2$, where $R^{13}$ is a $C_1$–$C_{10}$-hydrocarbon radical such as $C_1$–$C_{10}$-alkyl or $C_6$–$C_{10}$-aryl, and p is preferably 4. The carbon-bridged biscyclopentadienyl compound can be used as a mixture of isomers.

Carbon-bridged biscyclopentadienyl metallocene halides of the formula V can be converted into the corresponding monoalkyl or dialkyl compounds by literature methods, e.g. by reaction with alkylating agents such as lithium alkyls, (J. Am. Chem. Soc. 1973, 95, 6263).

The carbon-bridged biscyclopentadienyl metallocenes of the formula V can be formed as a mixture of the racemic form and the meso form. The separation of the isomeric forms, in particular the removal of the meso form, is known in principle (AU-A-31478/89; J. Organomet. Chem. 1988, 342, 21; EP-A 284 707) and can be carried out by extraction or recrystallization using various solvents.

The process of the invention allows the simple preparation of carbon-bridged biscyclopentadienyl metallocenes in high yield.

The carbon-bridged biscyclopentadienyl metallocenes obtainable using the metallocene preparation process of the invention can, together with a cocatalyst, be used as highly active catalyst components, e.g. for the preparation of olefin polymers.

It is possible to polymerize olefins, in particular those of the formula $R^a$—CH=CH—$R^b$, where $R^a$ and $R^b$ are identical or different and are each a hydrogen atom or a hydrocarbon radical having from 1 to 20 carbon atoms. $R^a$ and $R^b$ can also, together with the carbon atoms connecting them, form a ring. Examples of such olefins are ethylene, propylene, 1-butene, 1-hexene, 1-octene, 4-methyl-1-pentene, 1,3-butadiene, isoprene, norbornene, dimethanooctahydronaphthalene or norbornadiene. In particular, propylene and ethylene can be homopolymerized, ethylene can be copolymerized with a $C_3$–$C_{20}$-olefin and/or a $C_4$–$C_{20}$-diene or ethylene can be copolymerized with a cycloolefin.

The polymerization can be a homopolymerization or a copolymerization and can be carried out in solution, in suspension or in the gas phase, continuously or batchwise, in or more stages, at a temperature of from 0° to 200° C., preferably from 30° to 100° C.

In principle, a suitable cocatalyst in the polymerization is any compound which, owing to its Lewis acidity, can convert the neutral metallocene into a cation and stabilize the latter ("labile coordinatorion"). In addition, the cocatalyst or the anion formed therefrom should undergo no further reactions with the cation formed (EP 427 697). As cocatalyst, preference is given to using an aluminum compound and/or boron compound.

Cocatalysts used are preferably aluminoxanes (EP-A 129–368, Polyhedron 1990, 9, 429). In place of or in addition to an aluminoxane, it is possible to use boron compounds, in particular of the formulae $R_xNH_{4-x}BR_4'$, $R_xPH_{4-x}BR_4'$, $R_3CBR_4'$ or $BR_3'$, as cocatalysts. In these formulae, x is an integer from 1 to 4, preferably 3, the radicals R are identical or different, preferably identical, and are $C_1$–$C_{10}$-alkyl, $C_6$–$C_{18}$-aryl or 2 radicals R together with the atoms connecting them form a ring, and the radicals R' are identical or different, preferably identical, and are $C_6$–$C_{10}$-alkyl or $C_6$–$C_{18}$-aryl which can be substituted by alkyl, haloalkyl or fluorine (EP-A 277 003, 277 004, 426 638, 427697).

It is possible to preactivate the metallocene with a cocatalyst, in particular an aluminoxane, prior to use in the polymerization reaction. This can significantly increase the polymerization activity. The preactivation of the metallocene is preferably carried out in solution. Here, the metallocene is preferably dissolved in a solution of the aluminoxane in an inert hydrocarbon. Suitable inert hydrocarbons are aliphatic or aromatic hydrocarbons. Preference is given to using toluene.

To remove catalyst poisons present in the olefin, purification using an aluminum compound, preferably an aluminum alkyl such as trimethylaluminum or triethylaluminum, is advantageous. This purification can either be carried out in the polymerization system itself or the olefin is, prior to addition to the polymerization system, brought into contact with the aluminum compound and subsequently separated off again.

As molecular weight regulator and/or to increase the catalyst activity, hydrogen can be added in the polymerization process. This enables low molecular weight polyolefins such as waxes to be obtained.

The metallocene is preferably reacted with the cocatalyst outside the polymerization reactor in a separate step using a suitable solvent. Application to a support can be carried out during this step.

In the process, a prepolymerization can be carried out by means of the metallocene. The prepolymerization is preferably carried out using the (or one of the) olefin(s) used in the polymerization.

The catalyst used for the olefin polymerization can be supported. The application to a support allows, for example, the particle morphology of the polymer prepared to be controlled. The metallocene can be reacted first with the support and subsequently with the cocatalyst. The cocatalyst can also first be supported and subsequently reacted with the metallocene. It is also possible to support the reaction product of metallocene and cocatalyst. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can, for example, be carried out as described in EP 567 952.

Preferably, the cocatalyst, e.g. aluminoxane, is applied to a support such as silica gels, aluminum oxides, solid aluminoxane or other inorganic support materials such as magnesium chloride or else a polyolefin powder in finely divided form and is then reacted with the metallocene.

If the polymerization is carried out as a suspension or solution polymerization, an inert solvent customary for the Ziegler low-pressure process is used. For example, the polymerization is carried out in an aliphatic or cycloaliphatic hydrocarbon; examples which may be mentioned are propane, butane, hexane, heptane, isooctane, cyclohexane, methylcyclohexane. Furthermore, a petroleum or hydrogenated diesel oil fraction can also be used. It is also possible to use toluene. Preference is given to carrying out the polymerization in the liquid monomer.

Use of hydrogen or increasing the polymerization temperature also makes it possible to obtain polyolefins of low molecular weight, for example waxes, whose hardness or melting point can be varied by means of the comonomer content. Selection of the polymerization process and the type(s) of comonomer(s), and also the amount(s) of comonomer(s), enable olefin copolymers having elastomeric properties, e.g. ethylene/propylene/1,4-hexadiene terpolymers, to be prepared.

The following examples illustrate the invention.

1) 2,2-Bisindenylpropane 100.0 g (0.86 mol) of indene are dissolved in 400 ml of toluene and a solution of 86.2 g (2.2 mol) of sodium hydroxide and 19.6 g (86 mmol) of triethylbenzylammonium chloride in 86.2 ml of water (50% strength NaOH solution) is then added. The addition of 25.0 g (0.43 mol) of acetone is carried out dropwise over a period of 30 minutes. After a reacting time of 5 hours, the aqueous phase is separated off, extracted twice with 100 ml each time of diethyl ether and the combined organic phases are dried over $MgSO_4$. The solvent is removed under reduced pressure and the crude product is purified by recrystallization from toluene/hexane. This gives 99.6 g of 2,2-bisindenylpropane in 85% yield in the form of a yellow powder.

$^1$H-NMR (200 MHz, $CDCl_3$): 7.4–6.9 (m, 8H, arom. H), 6.42 (s, 2H, olefin. H), 3.35 (s, 4H, $CH_2$), 1.70 (s, 6H, $CH_3$). Mass spectrum: 272 M$^+$, correct disintegration pattern.

2) 1,1-Bisindenylethane 100.0 g (0.86 mol) of indene are dissolved in 400 ml of toluene and a solution of 86.2 g (2.2 mol) of sodium hydroxide and 19.6 g (86 mmol) of triethylbenzylammonium chloride in 86.2 ml of water (50% strength NaOH solution) is then added. The addition of 18.9 g (0.43 mol) of acetaldehyde is carried out dropwise over a period of 30 minutes. After a reaction time of 5 hours, the aqueous phase is separated off, extracted twice with 100 ml each time of diethyl ether and the combined organic phases are dried over MgSO$_4$. The solvent is removed under reduced pressure and the crude product is purified by recrystallization from toluene/hexane. This gives 91.5 g of 1,1-bisindenylethane in 82% yield in the form of a yellow powder.

$^1$H-NMR (200 MHz, CDCl$_3$): 7.3-6.9 (m, 8H, arom. H), 6.47 (s, 2H, olefin H), 3.41 (s, 4H, CH$_2$), 3.10 (s, 1H, CH), 1.65 (s, 3H, CH$_3$). Mass spectrum: 259 M$^+$, correct disintegration pattern.

3) Isopropylidenebis(1-indenyl)zirconium dichloride

A solution of 10 g (37 mmol) of 2,2-bisindenylpropane in 30 ml of diethyl ether is admixed at room temperature under argon protection with 29.6 ml (74 mmol) of a 2.5M butyllithium solution in hexane and stirred overnight. After addition of 20 ml of hexane, the beige suspension is filtered and the residue is washed with 20 ml of pentane. The dilithio salt is dried in an oil pump vacuum and then added at −78° C. to a suspension of 8.6 g (37 mmol) of ZrCl4 in dichloromethane. The mixture is warmed to room temperature over a period of 1 hour and stirred for a further 30 minutes at this temperature. After taking off the solvent, the orange-brown residue is extracted with 50 ml of toluene. Taking off the solvent gives 8.8 g (55%) of an orange powder. The ratio of racemate to meso form was determined as 2:1. Recrystallization from toluene enable 4.1 g (26%) of the pure racemate to be obtained.

$^1$H-NMR (200 MHz, CDCl$_3$): 7.8-6.9 (m, 8H, arom. H), 6.72 (m, 2H, Cp-H), 6.17 (m, 2H, Cp-H), 2.15 (s, 6H, CH$_3$). Mass spectrum: 432 M$^+$, correct disintegration pattern.

We claim:

1. A process for preparing a carbon-bridged biscyclopentadiene compound which comprises reacting one or two cyclopentadiene compounds, of which at least one cyclopentadiene compound is a substituted cyclopentadiene compound, with a carbonyl compound in the presence of at least one base and at least one phase transfer catalyst.

2. The process as claimed in claim 1, wherein the process is carried out in a multiphase system.

3. The process as claimed in claim 1, wherein the process is carried out in a two-phase system comprising an organic solvent and water.

4. The process as claimed in claim 1, wherein the base is a hydroxide of an element of group Ia, IIa or IIIa of the Periodic Table of the Elements.

5. The process as claimed in claim 1, wherein the phase transfer catalyst is a quaternary ammonium salt, a quaternary phosphonium salt or a crown compound.

6. The process as claimed in claim 1, wherein the carbon-bridged biscyclopentadiene compound has the formula I

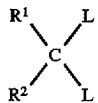

where L are, independently of one another, identical or different cyclopentadiene groups, where at least one group L is substituted cyclopentadienyl group, and R$^1$ and R$^2$ are identical or different and are each a hydrogen atom or a C$_1$–C$_{30}$-hydrocarbon radical or R$^1$ and R$^2$ together with the atoms connecting them form a ring system.

7. The process as claimed in claim 1, wherein, in formula I, both cyclopentadiene groups L are substituted cyclopentadiene groups.

8. The process as claimed in claim 7, wherein both cyclopentadiene groups L are identical.

9. The process as claimed in claim 6, wherein the groups L are identical and are tetramethylcyclopentadiene, 3-methylcyclopentadiene, 3-tert-butylcyclopentadiene, methyl-tert-butylcyclopentadiene, isopropylcyclopentadiene, dimethylcyclopentadiene, trimethylcyclopentadiene, trimethylethylcyclopentadiene, 3-phenylcyclopentadiene, diphenylcyclopentadiene, indene, 2-methylindene, 2-ethylindene, 3-methylindene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenaphthindene, 2-methyl-4,6-diisopropylindene, fluorene, 2-methylfluorene or 2,7-di-tert-butylfluorene.

10. The process as claimed in claim 6, wherein one or both of the cyclopentadiene groups L is 2-methylindene, 2-ethylindene, 3-methylindene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenanaphthindene, 2-methyl-4,6-diisopropylindene or a fluorenyl derivative such as fluorene, 2-methylfluorene or 2,7-di-tert-butylfluorene and R$^1$ and R$^2$ are identical and or a C$_1$–C$_{10}$-alkyl or C$_6$–C$_{14}$-aryl or the radicals R$^1$ and R$^2$ together with the atoms connecting them, form a ring system which contains from 4 to 40 carbon atoms.

11. The process as claimed in claim 6, wherein the carbon-bridged is cyclopentadienyl compound of formula I selected from the group consisting of 2,2-bisindenylpropane, 2,2-bisindenylbutane, 2,2-bisindenylmethane, 2,2-bisindenylcyclopentane, 2,2-bisindenylcyclohexane, 1,1-bisindenyl-1-phenyl-ethane, 1,1-bisindenylethane, 1,1-bisindenylpropane, 2,2-bis(2'-methyl-4'-phenylindenyl)propane, 2,2-bis(2'-ethyl-4'-phenyl-indenyl)propane, 2,2-bis(2'-methyl-4'-naphthylindenyl)propane, 2,2-bis(2'-methyl-4',5'-benzoindenyl)propane, 1,1-bis(2'-methyl-4'-phenylindenyl)-1-phenylethane, 1,1-bis(2'-ethyl-4'-phenyl-indenyl)-1-phenylethane, 1,1-bis(2'-methyl-4'-naphthylindenyl)-1-phenylethane, 2,2-biscyclopentadienylbutane, 2,2-bis(methyl-cyclopentadienyl)propane, 2-cyclopentadienyl-2-fluorenylpropane, 2-(3'-methylcyclopentadienyl)-2-fluorenylpropane, 2-indenyl-2-fluorenylpropane, 2-cyclopentadienyl-2-indenylpropane, 1-cyclopentadienyl-1-fluorenyl-1-phenylethane, 1-indenyl-1-fluorenyl-1-phenylethane, 2-(3'-tert-butylcyclopentadienyl)-2-fluorenylpropane and 1-cyclopentadienyl-1-indenyl-1-phenylethane.

12. The process as claimed in claim 6, wherein carbonyl compound is acetone or acetaldehyde, and the base is an hydroxide of an element of group Ia, IIa or IIIa of the Periodic Table of the Elements and the phase transfer catalyst is a quaternary ammonium salt, a quaternary phosphonium salt or a crown compound.

13. The process as claimed in claim 11, wherein carbonyl compound is acetone or acetaldehyde, and the base is an hydroxide of an element of group Ia, IIa or IIIa of the Periodic Table of the Elements and the phase transfer catalyst is a quaternary ammonium salt, a quaternary phosphonium salt or a crown compound.

14. The process as claimed in claim 11, wherein the carbonyl compound is selected from the group consisting of acetone, acetophenone, benzophenone, cyclo-hexanone, cyclopentanone, 2-hexanone, 2-butanone, 2-methyl-3-pentanone or 2,2-dimethyl-3-butanone or aldehydes such as acetaldehyde, 2,2-dimethyl-3-butanone, acetaldehyde and benzaldehyde and the base is LiOH, NaOH or KOH.

15. The process as claimed in claim 13, wherein the carbonyl compound is selected from the group consisting of acetone, acetophenone, benzophenone, cyclo-hexanone, cyclopentanone, 2-hexanone, 2-butanone, 2-methyl-3-pentanone or 2,2-dimethyl-3-butanone or aldehydes such as acetaldehyde, 2,2-dimethyl-3-butanone, acetaldehyde and benzaldehyde and the base is LiOH, NaOH or KOH.

16. A process for preparing a carbon-bridged biscyclopentadienyl metallocene, comprising the steps:
   a) preparing a carbon-bridged biscyclopentadiene compound by the process as claimed in of claim 1, and
   b) reacting the carbon-bridged biscyclopentadiene compound obtained in step a) with a metal compound $M^1X_p$, where $M^1$ is an element of group IIIb, IVb, Vb or VIb of the Periodic Table of the Elements, X is a $C_1$–$C_{40}$-radical, a halogen or a pseudohalogen and p is an integer from 0 to 4, under conditions under which the carbon-bridged biscyclopentadiene compound obtained in step a) is complexed to give the carbon-bridged biscyclopentadienyl metallocene.

17. The process for preparing a carbon-bridged biscyclopentadienyl metallocene of the formula V

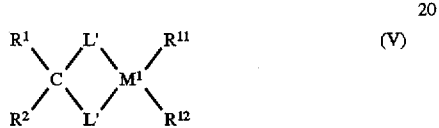

where $M^1$ is an element of group IIIb, IVb, Vb or VIb of the Periodic Table of the Elements, where L' are, independently of one another, identical or different cyclopentadiene groups, where at least one cyclopentadiene group L' is a substituted cyclopentadiene group, $R^1$ and $R^2$ are identical or different and are each hydrogen or a $C_1$–$C_{30}$-hydrocarbon radical, or the radicals $R^1$ and $R^2$ together with the atoms connecting them form a ring, and $R^{11}$ and $R^{12}$ are identical or different and are each hydrogen, a halogen atom or a $C_1$–$C_{40}$-radical which comprises the step of
   a) preparing a carbon-bridged biscyclopentadiene compound as is claimed in claim 1, and
   b) reacting the carbon-bridged biscyclopentadiene compound obtained in step a) with a metal compound $M^1X_p$, where $M^1$ is an element of group IIIb, IVb, Vb or VIb of the Periodic Table of the Elements, X is a $C_1$–$C_{40}$-radical and or $NR^{13}_2$, where $R^{13}$ is a $C_1$–$C_{20}$-hydrocarbon radical or $C_6$–$C_{16}$-aryl, a halogen or a pseudohalogen and p is an integer from 0 to 4, under conditions under which the carbon-bridged biscyclopentadiene compound obtained in step a) is complexed to give the carbon-bridged biscyclopentadienyl metallocene.

18. A process for preparing a carbon-bridged cyclopentadienyl metallocene comprising the steps of:
   a) reacting one or two cyclopentadiene compounds, of which at least one cyclopentadiene compound is a substituted cyclopentadiene compound, with a carbonyl compound in the presence of at least one base and at least one phase transfer catalyst to give a carbon-bridged biscyclopentadiene compound, and
   b) reacting the carbon-bridged biscyclopentadiene compound obtained in step a) with a metal compound $M^1X_p$, where $M^1$ is an element of group IIIb, IVb, Vb or VIb of the Periodic Table of the Elements, X is a $C_1$–$C_{40}$-radical and or $NR^{13}_2$, where $R^{13}$ is a $C_1$–$C_{20}$-hydrocarbon radical or $C_6$–$C_{16}$-aryl, a halogen or a pseudohalogen and p is an integer from 0 to 4, under conditions under which the carbon-bridged biscyclopentadiene compound obtained in step a) is complexed to give the carbon-bridged biscyclopentadienyl metallocene.

* * * * *